US006821394B2

(12) United States Patent
Shi

(10) Patent No.: US 6,821,394 B2
(45) Date of Patent: Nov. 23, 2004

(54) PROCESS OF EXTRACTING FROM HAW-PIT BY DRY DISTILLATION AND ITS DEVICE

(76) Inventor: Yi Shi, No. 420 Building 1, No. 1 De Wai Jiaochangkou Street, Xicheng District, Beijing 100011 (CN)

(*) Notice: Subject to any disclaimer, the term of this patent is extended or adjusted under 35 U.S.C. 154(b) by 0 days.

(21) Appl. No.: 10/311,461
(22) PCT Filed: Jun. 15, 2001
(86) PCT No.: PCT/CN01/00971
§ 371 (c)(1), (2), (4) Date: Apr. 21, 2003
(87) PCT Pub. No.: WO01/97864
PCT Pub. Date: Dec. 27, 2001

(65) Prior Publication Data
US 2003/0159914 A1 Aug. 28, 2003

(30) Foreign Application Priority Data
Jun. 16, 2000 (CN) .......................................... 00109230

(51) Int. Cl.⁷ .............................. B01D 3/14; B01D 3/42; A61K 35/78; A01N 65/00
(52) U.S. Cl. .............................. 203/2; 159/29; 159/40; 202/172; 202/186; 202/204; 203/49; 203/87; 203/73; 203/DIG. 14; 203/DIG. 11; 424/123; 424/777; 210/737
(58) Field of Search .............................. 203/2, 87, 49, 203/73, 100, DIG. 11, DIG. 14; 159/29, 40; 202/172, 204, 186; 210/265, 737; 422/1; 426/485, 321, 639; 424/123, 777; 134/25.3, 6, 32

(56) References Cited
U.S. PATENT DOCUMENTS 5,534,280 A * 7/1996 Welch ........................ 426/321
5,773,241 A * 6/1998 Ericsson ...................... 435/41
6,357,456 B2 * 3/2002 Segers ........................ 134/25.3
6,613,366 B1 * 9/2003 Fitzpatrick .................... 426/61

FOREIGN PATENT DOCUMENTS

| CN | A 1041281 | 4/1990 |
| CN | 96120686.1 | 11/1996 |
| CN | A 1182538 | 5/1998 |

OTHER PUBLICATIONS

China J. Medical Industry, 1996, 27(9) Li Anlin, "Preparation of Distillate Oil from Haw–Pit by Dry Distillation", P7–9.

Copy of International Search Report issued Sep. 13, 2001 (On Order).

* cited by examiner

Primary Examiner—Virginia Manoharan
(74) Attorney, Agent, or Firm—Greenberg Traurig, LLP

(57) ABSTRACT

The present invention relates to a process of extracting haw pits by dry distillation and the device used therein. The process includes the following steps: removing the impurities of haw pits and drying them; immersing haw pits in water and then dripping and charging the dried pit into the furnace for dry distillation; gradually raising the temperature and dry distilling the haw pits at two temperature ranges of 105–195° C. and 305–380° C. respectively and collecting the distillate; mixing together the distillate, allowing them to separate into layers by specific gravity difference and separating out the final brownish red transparent liquor by siphon. The method of the present invention can provide high yield of extraction and the present device is simple in structure. Further, the present invention is easy to be employed on the industrial scale.

17 Claims, 1 Drawing Sheet

PROCESS OF EXTRACTING FROM HAW-PIT BY DRY DISTILLATION AND ITS DEVICE

FILED OF INVENTION

The present invention relates to a processing technique of fruit pits, especially to a method and device of extracting the liquor from haw pits (herein, it is also referred as to "haw seed").

BACKGROUND OF THE TECHNOLOGY

Haw is a favorited and sour-tasted fruit for many people. They are planted in many northern provinces of China. They can be processed into many kinds of food according to one's taste. Haw pits, however, have seldom been properly utilized and sometimes they are burned as a fuel. This situation is really a pity.

It has been confirmed by modern scientific methods that liquor extracted from haw pits possesses unexpected antibacterial, disinfectant and sterilizing functions. In addition, they have already been widely used in the fields of medicine, hygiene, food processing and environmental protection. For example, external skin disinfectant prepared by using haw pits extract as the raw material does not irritate the skin mucous membrane and does not have any adverse reactions. Mosquito-repellent incense made of haw pits extract possesses good mosquito-killing effect and does not have any undesirable effect to human body. Along with the development of science and technology, the fields of application for haw pits extract would gradually been widened.

Up to now, the technical method for the dry distillation of haw pits such as that disclosed in Chinese Patent Applied No. 96120686.1 described the process of dry distillation of haw pits. Due to the limitation of technological conditions, the efficiency of dry distillation in the said Patent was not high enough and the percentage of corrosive and toxic component of phenol approached 20–25%. For the moment, the widely concerned problems of the manufacturing community are the following: how to utilize reasonable extracting process and simpler manufacturing device to raise the yield of the haw pits extract. At the same time, the undesirable and toxic components of the dry distillation extract should be lowered. These are right problems to be solved by the present invention.

OBJECTIVE OF THE PRESENT INVENTION

The objective of the present invention is to provide a method of extracting liquor from haw pits by dry distillation, which is simple and have high efficiency of extraction. In addition, the resulting product has very good bacteria-killing property and low content of harmful components.

Another objective of this invention is to provide a device for dry distillation extracting liquor from haw pits.

DISCLOSURE OF THE INVENTION

The method of the present invention for extracting haw pits by dry distillation consists of the following steps:

(1) Removing the impurities from the haw pits and drying the haw pits;

(2) Soaking haw pits in water and putting them into a dry distillation furnace after removing the water by dripping.

(3) In the first substep, raising the temperature within the temperature range of 105–195° C. stage by stage and maintaining the temperature at each stage; and in the second substep raising the temperature within the temperature range of 305–380° C. stage by stage and maintaining the temperature at each stage; and condensing and collecting the resulting distillate in the two substeps;

(4) Combining the distillates, setting aside for separation by different specific gravities, and separating the brownish red transparent liquid by siphon method.

Since most of the haw pits collected nowadays contain many impurities such as the residual fruit pulp, branches and leaves, coke, coal and garbage, they should be strictly removed in order to ensure the quality of the dry distillation liquor. In the above-mentioned step (1), the impurities can be removed by various methods such as sieving, specific gravity method and chemical method. Generally the pits are dried in natural environment.

In step (2), the haw pits were immersed in water whose volume was 1–2 times of that of the pits for 12–24 hours. Water will swell the pits and will be absorbed by the pits. This can raise the yield of the distillate and can further remove the contaminated soil and other impurities.

In step (3), in the first stage, the temperature of the furnace was raised to 105° C. and kept constant for one hour and then successively to 115° C., 135° C., 155° C., 175° C., 195° C. and kept at each temperature for one hour respectively. In the second stage, the temperature of the furnace was raised to 305° C. and kept constant for one hour and then successively to 325° C., 345° C., 365° C. and kept at each temperature for one hour respectively. By so doing, the decomposition of low boiling point distillate can be effectively avoided. When fine particle sand was added into the furnace at an amount of ½ to ¼ by weight based on the weight of the pits, they can improve the heat conduction of the system and raise the efficiency of the dry distillation. Further, the sand can be reused after cleaning.

Dry distillation can be carried out at atmospheric pressure or at reduced pressure. The heat sources used in the dry distillation include but not limited to direct fire or flue gas. And coal (a coal furnace should be installed outside the present furnace when using coal as heat source), coal gas, natural gas or electrical heater can be used to generate heat. Among them, flue gas heating is preferred.

The liquor obtained by dry distillation can be further subjected to fractional distillation. It is preferred to pass nitrogen gas into the fractionated liquor during the fractional distillation to protect the distillate from oxidizing.

The device for dry distilling haw pits of the present invention substantially consists of furnace body, porous inner pipe, eduction pipe, condensing pipe and condenser. The porous inner pipe was inserted into the haw pits, and another end of the porous inner pipe was connected to the eduction pipe. The eduction pipe was connected to the condensing pipe. And then the inner pipe, the eduction pipe, and the condensing pipe formed a passage. From the passage, the distillate obtained by the dry distillation can flow out of the present device.

The inner pipe was a round pipe with porous wall and open ends. It was situated in the center of the furnace and was surrounded by the raw material haw pits. Of course, multiple inner pipes can be placed in parallel and were connected to the eduction pipe and condensing pipe respectively to form a passage for the yield. The condensing pipe used can be of snake form, spiral plate form or butterfly form. The furnace body can be rotated in order to obtain more homogeneous heating and higher heating efficiency.

DETAILED DESCRIPTION OF THE PREFERRED EMBODIMENTS

Figure 1:
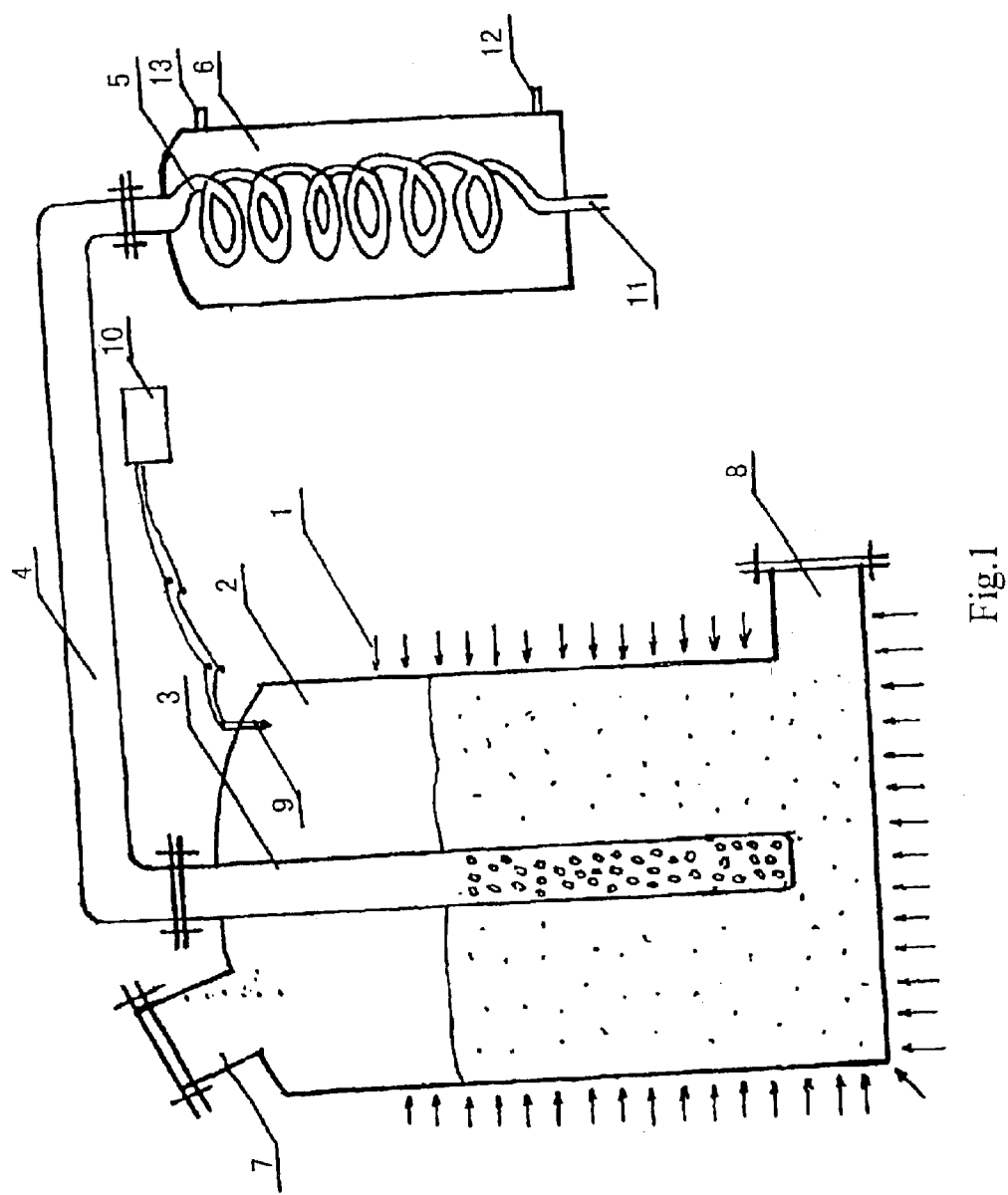
FIG. 1 is a schematic view of the present invention.

A more complete appreciation of the invention will be readily obtained by reference to the following description of the preferred embodiments and the accompanying drawings.

As illustrated in FIG. 1, 1 is the heat source which can be produced from, for example, coal, natural gas or electrical heater, 2 is the furnace body, 3 is the inner pipe, 4 is the eduction pipe, 5 is the condensing pipe, 6 is the condenser, 7 is the inlet for the raw material haw pits, 8 is the exit for the residual extracted haw pits, 9 is the thermometer, 10 is the displaying device of the thermometer, 11 is the outlet for the haw pits extracts, 12 is the inlet for cooling water and 13 represents the outlet for cooling water.

Furnace body should be made of carbon steel or titanium steel with a thickness of 6–10 mm. The permeation hole on the inner pipe should have a dimension smaller than those of the haw pits (preferably 2–3 mm) so as to prevent any haw pits around the inner pipe entering into the inner pipe through them. If only one inner pipe was used, it should be placed in the center of the furnace body. According to one embodiment of the present invention, the furnace body has a height of 1.8 meter and a diameter of 1 meter, the diameter of the inner pipe is 10–15 cm, the diameter of the inlet for raw material is 20 cm, the diameter of the outlet for distillate is 25 cm, the condenser has a height of 80 cm and a diameter of 30 cm, and the initial diameter of the condensing pipe is 10 cm and the diameter of the condensing pipe gradually becomes thinner and thinner from the initial portion to the end portion. The condensing pipe is in the shape of snake, spiral plate or butterfly.

Flange type couplings are used at the inlet 7, outlet 8, and also used for connecting the eduction pipe 4 with the inner pipe 3, and for connecting the eduction pipe 4 with the condensing pipe 5. All these couplings are sealed with asbestos pads. The above-mentioned dry distillation furnace can treat about 350 kilograms of haw pits once.

Gas chromatography coupled with mass spectroscopy (GC-MS) was used to analyze the distillate of the present invention. A total of 62 compounds were detected. They were mainly organic acids, carbonyl compounds, alcohols, esters and a small amount of phenols.

The said organic acids mainly include acetic acid, propionic acid, butyric acid, substituted butyric acid, acrylic acid, crotonic acid and the like.

The said aldehydes mainly include furyl carboxy aldehyde, furyl hydroxyl aldehyde, propionaldehyde, amyl aldehyde and the like.

The said ketones mainly include hydroxyketone, 2-acetone, butanone, hydroxyacetone and the like.

The said phenols mainly include 2-methoxy phenol, 2-methoxy-4-methyl phenol, phenol, 2,6-dimethoxyphenol and the like.

The said alcohols mainly include 2-amino propanol, benzyl alcohol and the like.

The total content of phenols was only 0.6%.

Most of the substances mentioned above have the function of sterilization and disinfection. The property of the distillate of the present invention was measured according to the "Standard for Disinfection, 3rd Ed.". When a solution of the present distillate of a concentration of 25% was used to kill colon bacillus, *staphylococcus aureus*, or *Candida albicans* for one minute, the efficiencies of sterilization, i.e., sterilizing rate, were 99.98%, 99.98% and 99.97% respectively. When a solution of the present distillate of a concentration of 20% was used to kill colon bacillus, *staphylococcus aureus*, or *Candida albicans* for 5 minutes, the efficiencies of sterilization were 99.92%, 99.92% and 99.90% respectively. The toxicity test on mice showed that all the oral administration $LD_{50}$ were higher than 5000 mg per 1 Kg body weight. In addition, the distillate does not irritate skin, eyes and mucous membrane of vagina.

The present method of extracting haw pits by dry distillation has the following advantages: the yield is higher, the distillate substantially does not contain highly corrosive and toxic phenol (the total content of phenols is only 0.6%), and it is easy to be employed on the industrial scale. The device needed by the present method is simple in structure, easy to be installed, low in cost and suitable to be industrialized.

The distillate of the present invention can be used in wide applications. The products derived from the present distillate include, but not limited to, wart eliminator, liquor for ringworm of feet and groin, drug for scalds, drug for bed-sore, vagina-cleaning liquor, mouth cleaning liquor, broad spectrum sterilant, drug for cardiovascular disease, Jie Ling Bao 774 drug, sterilizing incense, plant-based agricultural chemicals, food additives, HIV×AIDS drug, growth hormone for edible fungus, drug for hepatitis, healthy brewage or drink, cosmetics, first-aid package for battle field (external use).

EXAMPLE 350 kilograms of haw pits was washed clean, and the contaminated impurities, for example, the residual fruit pulp, branches, leaves and etc. after the processing of haw, were removed. The cleaned pits were dried in open air and left for further processing. Before the pits were charged into the furnace, they were soaked for 12–14 hours. The soaked haw pits were placed into a vessel with many holes to drip off the water. After about one hour, the pits were charged into the furnace to a height of about ⅔ of that of the furnace body, i.e., the other ⅓ part of the furnace body was left vacant. The furnace was then closed and fire was ignited to heat the furnace. The heat source used was flue gas. The heating process was gradual and was in two stages: In the first stage, the temperature of the furnace was raised to 105° C. and was kept at this temperature for one hour and then raised to 115° C., 135° C., 155° C., 175° C. and 195° C. and was kept at each temperature for 1 hour respectively while collecting the distillate. In the second stage, the temperature of the furnace was further raised to 305° C. and kept at this temperature for one hour and then raised to 325° C., 345° C. and 365° C. and kept at each temperature for 1 hour respectively to further collect the distillate. The distillates of the haw pits obtained in the two stages were mixed at a temperature which equals to or is lower than room temperature and at normal pressure. The mixed distillate was set aside to settle and separate into layers due to specific gravity difference. Brownish red transparent liquor was separated out by siphon.

The separated liquor was further fractionally distilled in the temperature range of 98–102° C. under normal pressure and $N_2$ bubbling (preferably, velocity of the $N_2$ flow was regulated to have only small bubbles). The number of the plates of the fractionating column used was 25 plates/meter. The fractional distillation was carried out intermittently for 12 hour. The final fractionally distilled liquor was pale yellow.

What is claimed is:

1. A method for dry distillation of haw pits, comprising:
removing impurities from the haw pits;

drying the haw pits;

soaking the haw pits in water;

removing the water and puffing the haw pits in a dry distillation furnace, the haw pits having a temperature;

raising the temperature of the haw pits to a first temperature value, the first temperature value being in a 105–195° C. range, to obtain a first extract;

condensing the first extract to provide a first distillate;

raising the temperature of the haw pits to a second temperature value, the second temperature value being in a 305–380° C. range, to obtain a second extract;

condensing the second extract to provide a second distillate;

collecting the first distillate and the second distillate;

combining the first distillate and the second distillate;

setting aside the combined first distillate and second distillate to separate the combined first distillate and second distillate into liquid layers by means of different specific gravities of the first distillate and the second distillate, thereby providing a brownish red transparent liquid layer; and separating the brownish red transparent liquid layer from the combined first distillate and second distillate.

2. The method of claim 1, wherein raising the temperature of the haw pits to a first temperature value is performed on a stage by stage manner.

3. The method of claim 2, wherein raising the temperature of the haw pits to a first temperature value is performed through a plurality of stage temperatures, each stage temperature being kept constant for a stage time of one hour.

4. The method of claim 3, wherein the plurality of stage temperatures comprises a first stage temperature value of 115° C., a second stage temperature value of 135° C., a third stage temperature value of 155° C., a fourth stage temperature value of 175° C., and a fifth stage temperature value of 195° C.

5. The method of claim 1, wherein raising the temperature of the haw pits to a second temperature value is performed on a stage by stage manner.

6. The method of claim 5, wherein each stage comprises raising the temperature to a stage temperature, the stage temperature kept constant for a stage time of one hour.

7. The method of claim 6, wherein raising the temperature of the haw pits to a second temperature value, comprises the first stage, second stage, third stage and fourth stage the stage temperature values being of 305° C., 325° C., 345° C. and 365° C. for the first stage, second stage, third stage and fourth stage respectively.

8. The method of claim 1, wherein soaking the haw pits in water comprises soaking the haw pits in a volume ratio of water to haw pits of 1:2 for a soaking time of 12–24 hours.

9. The method of claim 1, wherein removing the water is performed by dripping.

10. The method of claim 1, wherein fine sand particles are added into the furnace at a ½ to ¼ weight ratio of the sand particles to the haw pits.

11. The method of claim 1, wherein said dry distillation is carried out under normal pressure or under reduced pressure.

12. The method of claim 1, wherein the furnace is a furnace heated by fire directly or by flue gas.

13. The method according to claim 1, wherein, the separated brown red transparent liquid is further subjected to fractional distillation at the temperature range of 98–102° C. by passing of nitrogen gas into the separated brown red transparent liquid.

14. A device for dry distillation of haw pits, which consists essentially of:

a furnace body;

a porous inner pipe having an inner pipe first end and an inner pipe second end;

an education pipe having an eduction pipe first end and an education pipe second end;

a condensing pipe having a condensing pipe first end and a condensing pipe second end; and a condenser, the inner pipe first end inserted in the furnace body, the inner pipe second end connected to the eduction pipe first end, the eduction pipe second end connected to the condensing pipe first end, the condensing pipe second end connected to a condenser, whereby a passage is formed by the inner pipe, the eduction pipe and the condensing pipe, and, in use, an extract from the haw pits flows through the passage, condenses, and flows our of the device as a distillate.

15. The device according to claim 14, wherein the education pipe second end is connected to the condensing pipe first end through at least two inner pipes forming a passage.

16. The device according to claim 14, wherein the condensing pipe has the shape of snake, spiral plate or butterfly.

17. The device according to claim 16, wherein the furnace body is rotatable.

* * * * *